United States Patent [19]
Torgerson et al.

[11] Patent Number: 6,165,455
[45] Date of Patent: Dec. 26, 2000

[54] PERSONAL CARE COMPOSITIONS CONTAINING THERMOPLASTIC ELASTOMERIC GRAFT COPOLYMERS

[75] Inventors: Peter Marte Torgerson, Washington Court House; Sanjeev Midha, Blue Ash, both of Ohio

[73] Assignee: The Procter & Gamble Company, Cincinnati, Ohio

[21] Appl. No.: 08/897,397

[22] Filed: Jul. 21, 1997

Related U.S. Application Data

[63] Continuation of application No. 08/445,267, May 19, 1995, abandoned, which is a continuation of application No. 08/269,246, Jun. 30, 1994, abandoned.

[51] Int. Cl.[7] ............................ A61K 7/075; A61K 31/74
[52] U.S. Cl. .......................................................... 424/70.12
[58] Field of Search .......................................... 424/70.12

[56] References Cited

U.S. PATENT DOCUMENTS

| | | | |
|---|---|---|---|
| 3,786,116 | 1/1974 | Milkovich et al. | 424/525 |
| 3,832,458 | 8/1974 | Merrill | 424/19 |
| 3,928,558 | 12/1975 | Cheesman et al. | 424/47 |
| 4,011,376 | 3/1977 | Tomalia et al. | 526/11.1 |
| 4,387,090 | 6/1983 | Bolich, Jr. | 424/70 |
| 4,659,777 | 4/1987 | Riffle et al. | 525/100 |
| 4,693,935 | 9/1987 | Mazurek | 428/352 |
| 4,699,941 | 10/1987 | Salerno | 524/308 |
| 4,761,198 | 8/1988 | Salerno | 156/334 |
| 4,888,406 | 12/1989 | Ohsugi et al. | 526/279 |
| 4,910,268 | 3/1990 | Kobayashi | 525/411 |
| 5,006,582 | 4/1991 | Mancinelli | 526/279 |
| 5,061,481 | 10/1991 | Suzuki et al. | 526/279 |
| 5,086,142 | 2/1992 | Fock et al. | 520/318 |
| 5,104,952 | 4/1992 | Babu | 526/279 |
| 5,106,609 | 4/1992 | Bolich, Jr. et al. | |
| 5,342,883 | 8/1994 | Jenkins et al. | 524/845 |
| 5,565,193 | 10/1996 | Midha et al. | 424/70.12 |
| 5,622,694 | 4/1997 | Torgerson et al. | 424/70.12 |
| 5,658,557 | 8/1997 | Bolich, Jr. et al. | 424/70.12 |

FOREIGN PATENT DOCUMENTS 0412707   2/1991   European Pat. Off. .

OTHER PUBLICATIONS

U.S. application No. 08/259,070, Torgerson & Midha, filed Jun. 20, 1994.
U.S. application No. 08/257,962, Torgerson & Midha, filed Jun. 16, 1994.
U.S. application No. 08/231,955, Torgerson & Midha, filed Apr. 21, 1994.
U.S. application No. 08/086,605, Torgerson & Midha, filed Jul. 1, 1993.
U.S. application No. 08/259,069, Torgerson & Midha, filed Jun. 20, 1994.
U.S. application No. 08/257,961, Torgerson & Midha, filed Jun. 16, 1994.
U.S. application No. 08/236,881, Torgerson & Midha, filed Apr. 29, 1994.
U.S. application No. 08/110,592, Torgerson & Midha, filed Aug. 23, 1993.
S. Shoda, "Synthesis and Surfactant of Copolymers Having a Poly (2–Oxazoline) Graft Chain," *Journal of Polymer Science,* vol. 30, 1489–1494 (1992).
T. Saegusa & Y. Chujo, "Macromolecular Engineering on the Basis of the Polymerization of 2–Oxazolines," *Makromol. Chem.,* Macromol. Symp. 51, 1–10 (1991).
Kobayashi et al., "Synthesis of Poly (ethylene–co–(vinyl acetate)–g–(2–alk,1–2–oxazolines),"*Polym, J.* (Tokyo), vol. 23/11 pp. 1307–1315, (1991).
Sinai–Zingde et al., "Polyoxazoline–Containing Copolymers as Emulsifiers for Polymer Blends," *Makromol. Chem.,* Macromol. Symp., #42/43, pp. 329–343, (1991).
Sinai–Zingde et al., "Polyoxazoline–containing Copolymers Useful as Emulsifiers for Polymer Blends," *Polymer Prepr.,* #31(1), pp. 63–65 (1990).
Kobayashi et al., "Synthesis and Polymerization of Poly(2–oxazoline) Macromonomers Having a Glycol Group," *Makromol. Chem.,* Rapid Cammun., #11(1), pp. 11–14, (1990).
Kobayashi, "Synthesis of Acryl– and Methacryl–type Macromonomers and Telechelics by Utilizing Living Polymerization of 2–Oxazolines," *Macromolecules* 1989, 22, pp. 2878–2884, (1989).
Miyamato, "End Capping of Growing Species of Poly(2–oxazoline)," *Macromolecules,* #22/4, pp. 1604–1607, (1989).
Riffle et al., "Narrow Distribution Oxazoline/Siloxane Copolymers," *Polymer Prepr.,* #29/2, pp. 93–96, (1988).

*Primary Examiner*—Peter F. Kulkosky
*Attorney, Agent, or Firm*—Stephen T. Murphy

[57] ABSTRACT

The present invention relates to hair care compositions containing nonpolar graft thermoplastic elastomeric copolymers and a water insoluble volatile solvent for the copolymer. This invention relates to styling products such as sprays and mousses, to hair conditioning products such as rinses and leave on conditioners, and to shampoo products useful for both cleansing and conditioning the hair.

24 Claims, No Drawings

PERSONAL CARE COMPOSITIONS CONTAINING THERMOPLASTIC ELASTOMERIC GRAFT COPOLYMERS

This is a file wrapper continuation of application Ser. No. 08/445,267, filed on May 19, 1995 abandoned, which is a file wrapper continuation of application Ser. No. 08/269,246, filed Jun. 30, 1994 (abandoned).

TECHNICAL FIELD

The present invention relates to hair care compositions containing nonpolar graft thermoplastic elastomeric copolymers and a water insoluble volatile solvent for the copolymer. This invention relates to styling products such as sprays and mousses, to hair conditioning products such as rinses and leave on conditioners, and to combination shampoo products useful for both cleansing and conditioning the hair.

BACKGROUND OF THE INVENTION

The use of polymeric materials in hair care products is of increasing importance. In the hair care area, polymers can be used for hair hold and setting products, for hair conditioning products, and in shampoos. Whereas a great many benefits can be obtained through the use of polymeric materials in these types of compositions, it remains desirable to further improve such compositions. For example, it would be desirable to provide products with improved style retention characteristics or with improved hair conditioning benefits.

In the hair care area, the desire to have hair retain a particular style or shape is widely held. Such style retention is generally accomplished by either of two routes: permanent chemical alteration of the hair fiber or temporary alteration of hair style or shape. A temporary alteration is one which can be removed by water or by shampooing. Temporary style alteration has generally been accomplished by application of a composition to dampened hair after shampooing and/or conditioning and prior to drying and/or styling. Products in the form of mousses, gels, lotions, or sprays are most commonly used for this purpose. Once the desired style is achieved, spray products are commonly used to help retain the style. These various hair care products utilize a variety of gums and resins for providing styling and retention. However, the gums and resins currently used tend to feel either too sticky or too stiff upon the hair. Also, these gums and resins do not wash out as easily as desired. Therefore, the need exists for improved styling and style retention materials which provide a strong, lasting, hold without being either too stiff or too sticky, and yet which are easily removed by shampooing. Furthermore, because most hair care styling compositions are water and/or alcohol based, it is necessary that these materials have good solubility or dispersibility in these bases.

Similarly in the hair conditioning area, it would be desirable to develop polymers which provide improved conditioning benefits and which can be delivered from a wide variety of matrices, including rinses, leave-on compositions, and shampoos. Many conventional conditioning agents have the disadvantage of leaving the hair feeling and looking coated. Also, many conventional conditioning agents are not suitable for delivery from a shampoo matrix, because they are removed from the hair during the washing process instead of remaining behind on the hair fibers.

Nonpolar, hydrophobic thermoplastic elastomeric copolymers are well known in the art, but have not been used for personal care applications, such as hair care products. See, e.g., U.S. Pat. No. 3,786,116, to Milkovich et al., issued Jan. 15, 1974. Thermoplastic elastomeric copolymers combine thermoplastic properties, which give them solubility and strength, with rubber-like elastic properties, which give them flexibility and shape retention. The thermoplastic elastomeric copolymers of the present invention are non-polar materials, being relatively insoluble in water and/or alcohol. These solubility characteristics makes these copolymers highly useful for formulation in hair care products.

It is also well known that polymers can be modified by the incorporation or grafting of silicone. See, e.g., U.S. Pat. No. 5,106,609, to R. E. Bolich Jr., et al. issued Apr. 21, 1992, and U.S. Pat. No. 4,693,935, to Mazurek, issued Sep. 15, 1987. Silicone grafted polymers tend to have a low surface energy and provide unique aesthetic and formulation advantages not usually obtained from non-silicone grafted polymers.

Despite the advantages that non-polar thermoplastic elastomeric copolymers can provide, these materials are generally difficult to formulate. It has been found, however, in the present invention that the use of certain insoluble volatile solvents provides a highly desirable basis for these compositions. The resulting compositions have good styling and conditioning performance and have a highly desirable feel upon the hair, e.g., they do not leave the hair feeling stiff or sticky.

It is an object of the present invention to provide hair care compositions containing nonpolar graft thermoplastic elastomeric copolymers.

It is another object of the present invention to provide hair care compositions having improved style and hold benefits.

It is another object of the present invention to provide novel hair care compositions having improved conditioning benefits.

These and other objects will become readily apparent from the detailed description which follows.

SUMMARY OF THE INVENTION

The present invention relates to a hair care composition, comprising:

(A). a thermoplastic elastomeric copolymer having a backbone and two or more hydrophobic polymeric side chains, said copolymer formed from the copolymerization of randomly repeating A, B, and C units wherein said copolymer comprises:

(i) from about 20% to about 90% by weight of said A units, wherein said A units are monomer units copolymerizable with said B and C units;

(ii) from about 10% to about 60% by weight of said B units, wherein said B units are hydrophobic macromonomer units having a polymeric portion and a moiety copolymerizable with said A and C units; and (iii) from 0% to about 20% by weight of said C units, wherein said C units are polysiloxane macromonomer units having a polymeric portion and a moiety copolymerizable with said A and B units, wherein said A units, in conjunction with said copolymerizable moieties of said B units and said C units, form said backbone; wherein said polymeric portion of said B units forms said hydrophobic side chains; wherein said copolymer has a weight average molecular weight greater than about 10,000, and wherein said copolymer exhibits at least two distinct $T_g$ values, said first $T_g$ corresponding to said backbone and having a value less than about 0° C., and said second $T_g$ corresponding to said hydrophobic polymeric side chains and having a value greater than about 25° C.; and (B). a water-insoluble, volatile solvent for said copolymer suitable for application to the hair.

The present invention also relates to a hair care composition, comprising:

(A). a thermoplastic elastomeric copolymer having a backbone and two or more hydrophobic polymeric side chains, said copolymer formed from the copolymerization of randomly repeating A, B, and C units and corresponding to the formula $$[A]_a[B]_b[C]_c$$

wherein A is at least one monomer unit copolymerizable with B and C selected from the group consisting of acrylic acid esters, N-alkyl acrylamides, alkyl vinyl ethers, alkyl substituted styrenes, and mixtures thereof, and a is an integer of about 100 or greater;

B is at least one nonpolar, hydrophobic macromonomer unit copolymerizable with A and C, corresponding to the formula

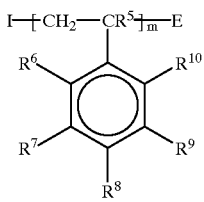

wherein I is selected from the group consisting of hydrogen, C1–40 straight or branched chain alkyl, benzyl, 1-phenyl substituted C2–40 straight or branched chain alkyl, 1,1-diphenyl substituted C2–40 straight or branched chain alkyl, and mixtures thereof; $R^5$ is selected from the group consisting of H and C1–C8 alkyl; $R^6$, $R^7$, $R^8$, $R^9$, and $R^{10}$ are independently selected from the group consisting of C1–C8 straight or branched chain alkyl such that each of $R^6$, $R^7$, $R^8$, $R^9$, and $R^{10}$ are not simultaneously H; m is an integer from about 10 to about 2000; E is an ethylenically unsaturated moiety, copolymerizable with A and C, selected from the group consisting of vinyl, allyl, acryloyl, methacryloyl, ethacryloyl, 2-vinylbenzoyl, 3-vinylbenzoyl, 4-vinylbenzoyl; 2-vinylbenzyl, 3-vinylbenzyl, 4-vinylbenzyl, 1-butenyl, 1-propenyl, isobutenyl, cyclohexenyl, cycolpentenyl, and mixtures thereof; and b is an integer of about 2 or greater;

C is a polysiloxane macromonomer unit copolymerizable with A and B corresponding to the formula $$E'(Y)_w Si(R^{11})_{3-t}(Z)_t$$

wherein E' is an ethylenically unsaturated moiety copolymerizable with A and B; Y is a divalent linking group; $R^{11}$ is selected from the group consisting of H, lower alkyl, aryl, or alkoxy; Z is a monovalent siloxane polymeric moiety having a number average molecular weight of at least about 500, is essentially unreactive under copolymerization conditions, and is pendant from said backbone after polymerization; w is 0 or 1; t is an integer from 1 to 3; and c is an integer of zero or greater; and (B). a water insoluble volatile solvent for said copolymer suitable for application to the hair.

In further embodiments, the B macromonomer can be a copolymeric macromonomer containing two or more different randomly repeating monomer units.

In further embodiments, the present invention relates to methods for styling and/or holding hair.

In further embodiments, the present invention relates to methods for conditioning the hair.

All percentages and ratios used herein are by weight of the total composition and all measurements made are at 25° C., unless otherwise designated. The invention hereof can comprise, consist of, or consist essentially of, the essential as well as optional ingredients and components described herein. All documents referred to herein, including all patents, patent applications, and printed publications, are hereby incorporated by reference in their entirety in this disclosure.

DETAILED DESCRIPTION OF THE INVENTION

The term "thermoplastic elastomeric copolymer" as used herein means that the copolymer has both thermoplastic and elastomeric properties. The term "thermoplastic elastomeric copolymer" is one familiar to those of ordinary skill in polymer science. By "thermoplastic" is meant that upon heating, the copolymer softens and upon cooling it rehardens; upon being subject to stress it begins to flow and upon removal of stress it stops flowing. By "elastomeric" is meant that the copolymer has an elastic modulus such that the copolymer exhibits a resistance to deformation and has limited extensibility and retraction. In other words, the copolymer tends to recover its size and shape after deformation.

"Grafted copolymers" is a term familiar to those of ordinary skill in polymer science and is used to describe copolymers onto which another chemical moiety has been added or "grafted", and means that these copolymers can contain pendant polymeric side chains, or in other words, these polymers can be formed from the "grafting" or incorporation of polymeric side chains onto or into the copolymer.

The term "macromonomer" is one familiar to those of ordinary skill in polymer science, and is used to describe a polymeric material containing a polymerizable moiety. In other words, a macromonomer is a macromolecular monomer, which is essentially a high molecular weight type of monomer building block unit which can be used in a polymerization reaction to form polymers with itself, with other monomers, or with other macromonomers.

The term "nonpolar" as used herein to describe the copolymers means that these copolymers are soluble in the water insoluble volatile solvent component described below. By "soluble" is meant that the copolymer is soluble in this solvent component at 25° C. at a concentration of at least about 20 mg/mL, more preferably about 50 mg/mL, and most preferably about 100 mg/mL.

The term "hydrophobic" is used herein in its standard meaning of lacking affinity for water.

Thermoplastic Elastomeric Copolymers

The hair care compositions of the present invention comprise a thermoplastic elastomeric copolymer. In general the hair care compositions comprise from about 0.1% to about 25%, preferably from about 0.5% to about 20%, and more preferably from about 1% to about 10%, and most preferably from about 2% to about 5%, by weight of the total composition, although higher or lower amounts can be used depending upon the application.

The copolymers of the present invention are characterized in having an elastomeric or flexible backbone; at least two thermoplastic, hydrophobic side chains; and optionally one or more polysiloxane chains. This combination of elastomeric, thermoplastic, and optional polysiloxane moieties in a single copolymer provides the unique and useful properties of these materials. The copolymers of the present invention, can also be referred to as "graft copolymers" because they can be prepared from the copolymerization of monomer units and macromonomer and optional polysiloxane units. In other words, the macromonomer and optional polysiloxane units are "grafted" or incorporated into the copolymer.

These copolymers exhibit at least two distinct immiscible phases. Without being limited by theory, it is believed that the hydrophobic thermoplastic side chains of these copolymers are closely associated with each other thereby existing in one phase, while the backbone of the copolymer remains in a separate phase. Depending on the relative percentage of polysiloxane moieties in the copolymers, the polysiloxane side chains can also form yet another distinct phase. A consequence of this phase immiscibility is that these copolymers exhibit at least two distinct glass transition temperatures or, "$T_g$'s", namely one $T_g$ for the backbone and one $T_g$ for the hydrophobic side chains formed by the B macromonomers. The copolymers can also exhibit a third glass transition temperature corresponding to the optional polysiloxane side chains. Whether such a third $T_g$ is observable will depend upon a number of factors including the percent silicone in the copolymer, the number of polysiloxane side chains in the copolymer, the temperature separation between each of the $T_g$'s involved, and other such physical factors.

$T_g$ is a well known term of art in polymer science used to describe the temperature at which a polymer or portion thereof undergoes a transition from a solid or brittle material to a liquid or rubber-like material. Glass transition temperatures can be measured using standard techniques that are well known to the polymer scientist of ordinary skill in the art. One particularly useful technique for determining glass transitions is differential scanning calorimetry (also known as DSC). The glass transition phenomenon in polymers is described in *Introduction to Polymer Science and Technology: An SPE Textbook*, (eds. H. S. Kaufman and J. J. Falcetta), (John Wiley & Sons: 1977), which is incorporated by reference herein in its entirety.

The $T_g$ of the backbone of the copolymers herein (i.e. that part of the copolymer not containing the hydrophobic side chains and the optional polysiloxane side chains) should be less than about 0° C. Preferably the $T_g$ of the backbone should be from about −10° C. to about −130° C., more preferably from about −20° C. to about −125° C., and most preferably from about −45° C. to about −120° C. The $T_g$ of the hydrophobic side chain of the copolymers (i.e. that part of the copolymer not containing the backbone and the optional polysiloxane side chains) is greater than about 20° C. Preferably the $T_g$ of the hydrophobic sidechain should be from about 25° C. to about 200° C., more preferably from about 30° C. to about 175° C., and most preferably from about 35° C. to about 150° C. The $T_g$ of the polysiloxane side chains of the copolymers (i.e. that part of the copolymer not containing the backbone and hydrophobic side chains) is approximately about −120° C. As described above, a distinct $T_g$ is not always observable for the optional polysiloxane side chains of these copolymers.

Because these copolymers possess at least two distinct $T_g$'s, for the backbone and the hydrophobic side chains of the B macromonomers, these copolymers are useful in hair conditioning, hair styling, and setting compositions. Additionally, the siloxane side chains of these copolymers provide a smooth silky, feel and shine to the hair.

The copolymers of the present invention are formed from the copolymerization of randomly repeating A, B, and C units, preferably wherein the A units are selected from at least one polymerizable, ethylenically unsaturated monomer unit; the B units are selected from at least one hydrophobic macromonomer unit which contains a polymeric portion and a copolymerizable moiety, preferably an ethylenically unsaturated moiety which is copolymerizable with the A and C units; and the C units, when optionally present, are selected from at least one polysiloxane macromonomer unit which contains a polymeric portion and a copolymerizable moiety, preferably an ethylenically unsaturated moiety which is copolymerizable with the A and B units. In preferred embodiments of these copolymers, the backbone is formed from the polymerization of the A monomer units with the ethylenically unsaturated portion of the hydrophobic B macromonomer unit, and the ethylenically unsaturated portion of the optional polysiloxane C macromonomer unit. The polymeric portion of the B macromonomer units forms the hydrophobic side chains of the copolymer. The polymeric portion of the optional C macromonomer units forms the polysiloxane side chains of the copolymer. The A, B, and C units can be selected from a wide variety of structures as long as the limitations of the copolymer are met (e.g., solubility, $T_g$'s, and molecular weights).

The A monomer units of the copolymers of the present invention comprise from about 20% to about 90%, more preferably from about 35% to about 85%, and most preferably from about 50% to about 80%, by weight, of the copolymers.

The hydrophobic B macromonomer units comprise from about 10% to about 60%, more preferably from about 20% to about 55%, and most preferably from about 30% to about 50%, by weight of the copolymers.

The optional C polysiloxane macromonomer units comprise from 0% to about 20%, more preferably from 0% to about 15%, and most preferably from 0% to about 10%, by weight of the copolymers.

The copolymers of the present invention have a weight average molecular weight of at least about 10,000. There is no upper limit for molecular weight except that which limits applicability of the invention for practical reasons, such as viscosity, processing, aesthetic characteristics, formulation compatibility, etc. The weight average molecular weight is less than about 5,000,000, more generally less than about 2,500,000, and typically less than about 1,500,000. Preferably, the weight average molecular weight is from about 10,000 to about 5,000,000, more preferably from about 75,000 to about 1,000,000, even more preferably from about 100,000 to about 850,000, and most preferably from about 125,000 to about 750,000.

Alternatively, the copolymers of the present invention can also be represented by the formula $$[A]_a[B]_b[C]_c$$

wherein A, B, and C are as described herein; and where a is an integer of about 100 or greater, preferably a is an integer from about 100 to about 3000, more preferably from about 250 to about 2000, and most preferably from about 350 to about 1500; b is an integer of about 2 or greater, preferably from about 2 to about 50, more preferably from about 2 to about 20, and most preferably from about 2 to about 10; and c is an integer of zero or greater, preferably from zero to about 25, more preferably from zero to about 10, and most preferably from zero to about 5. In this formula, it is expressly intended that even though ranges are provided for the subscripts a, b, and c, these subscripts are not intended to strictly limit the polymers herein so long as the physical properties, e.g., $T_g$, solubility, and the like, of the polymers are achieved. When the copolymers herein are described by the formula disclosed in this paragraph it has been found useful to describe the copolymers by their number average molecule weights. The number average molecular weight is less than about 2,500,000, more generally less than about 1,500,000, and typically less than about 1,000,000. Preferably, the number average molecular weight is from about 10,000 to about 1,000,000, more preferably from about 20,000 to about 500,000, and most preferably from about 25,000 to about 250,000.

As defined above, the copolymers useful herein are preferably nonpolar, having the indicated solubility characteristics. By appropriate selection and combination of the particular A, B, and optional C units, and by the choice of specific relative ratios of the units well within the ability of one of ordinary skill in the art, the copolymers can be optimized for various physical properties such as solubility, $T_g$'s, and the like, and for compatibility with other ingredients commonly used in hair care applications.

Monomer A Units

The A monomer unit is selected from copolymerizable monomers, preferably ethylenically unsaturated monomers. Either a single A monomer or combinations of two or more A monomers can be utilized. The A monomers are selected to meet the requirements of the copolymer. By "copolymerizable", as used herein, is meant monomers that can be copolymerized using any conventional synthetic techniques. Monomers that are copolymerizable using conventional free radical initiated techniques are preferred. The term "ethylenically unsaturated" is used herein to mean monomers that contain at least one polymerizable carbon—carbon double bond (which can be mono-, di-, tri-, or tetra-substituted).

The A monomer units of the copolymers of the present invention comprise from about 20% to about 90%, more preferably from about 35% to about 85%, and most preferably from about 50% to about 80%, by weight, of the copolymers.

A wide variety of unsaturated A monomer units can be used in the present invention, including mixtures of two of more monomers, so long as the $T_g$, molecular weight, and solubility requirements of the polymers are met. Nonlimiting classes of monomers useful herein include those selected from the group consisting of acrylic acid esters, N-alkyl acrylamides, alkyl vinyl ethers, and alkyl substituted styrenes.

The acrylic acid esters useful herein can be described by the following formula $$R^3-O-\overset{\overset{O}{\|}}{C}-CR^1=CHR^2$$

wherein $R^1$ and $R^2$ are independently selected from the group consisting of H, $C_1$–$C_8$ straight or branched chain alkyl, methoxy, ethoxy, 2-hydroxyethoxy, 2-methoxyethyl, and 2-ethoxyethyl, and $R^3$ is selected from the group consisting of $C_1$–$C_{30}$ straight chain, branched chain, or cyclic alkyl; chloro and/or fluoro substituted $C_1$–$C_{30}$ straight chain, branched chain or cyclic alkyl; phenyl substituted $C_1$–$C_{30}$ straight chain, branched chain, or cyclic alkyl; methoxy, ethoxy, and phenoxy substituted $C_1$–$C_{30}$ straight chain, branched chain, or cyclic alkyl; and cyano substituted $C_1$–$C_{30}$ straight chain, branched chain, or cyclic alkyl. Preferred is when $R^3$ is $C_1$–$C_{20}$ straight chain or branched chain alkyl. Nonlimiting examples of acrylic acid esters include 2-ethylhexyl acrylate, hexadecyl acrylate, octadecyl acrylate, pentyl acrylate, 2-phenyethyl acrylate, propyl acrylate, tetradecyl acrylate, tridecyl acrylate, 2-ethylhexyl methacrylate, 2-ethylhexyl ethacrylate, isopropyl acrylate, methoxybutyl acrylate, methylbutyl acrylate, methyl acrylate, heptyl acrylate, hexyl acrylate, methylpentyl acrylate, nonyl acrylate, phenoxyethyl acrylate, propyl acrylate, 1,1,1-trifluoroethyl acrylate, benzyl acrylate, butyl acrylate, cycohexyl acrylate, cyaonoethyl acrylate, dimethylbutyl acrylate, 1,1-dihydroperfluorohexyl acrylate, 1,1-dihydroperfluorodecyl acrylate, 1,1-dihydroperfluoropentyl acrylate, dimethyloctyl acrylate, dodecyl acrylate, ethylbutyl acrylate, ethyl acrylate, heptafluorobutyl acrylate, heptyl acrylate, hexadecyl acrylate, hexyl acrylate, isobutyl acrylate, isodecyl acrylate, and mixtures thereof. Preferred among these esters are those selected from the group consisting of octadecyl acrylate, tetradecyl acrylate, nonyl acrylate, ethyl butyl acrylate, ethyl acrylate, 2-ethylhexyl acrylate, hexadecyl acrylate, hexyl acrylate, and mixtures thereof.

The N-alkyl acrylamides useful herein can be described by the following formula $$X-\overset{\overset{O}{\|}}{C}-CR^1=CHR^2$$

wherein $R^1$ and $R^2$ are as previously described above and X is selected from the group consisting of —NHR$^4$, and —N(R$^4$)$_2$ wherein each $R^4$ is independently selected from the group consisting of $C_1$–$C_{30}$ straight or branched chain alkyl. Nonlimiting examples of amides useful herein include those selected from the group consisting of N-octyl acrylamide, N-octyl methacrylamide, N-octyl ethacrylamide, N,N-dimethyl acrylamide, N,N-dimethyl methacrylamide, N-(2-ethylhexyl) acrylamide, N-hexadecyl acrylamide, N,N-methylpropyl acrylamide, N,N-methylpropyl methacrylamide, and mixtures thereof.

The alkyl vinyl ethers useful herein can be described by the following formula $$R^3-O-CR^1=CHR^2$$

wherein $R^1$, $R^2$, and $R^3$ are all as previously described above. Nonlimiting examples of alkyl vinyl ethers useful herein include those selected from the group consisting of ethyl vinyl ether, decyl vinyl ether, hexadecyl vinyl ether, hexyl vinyl ether, isobutyl vinyl ether, isopropyl vinyl ether, octyl vinyl ether, propyl vinyl ether, s-butyl vinyl ether, and mixtures thereof.

The alkyl substituted styrenes useful herein can be described by the following formula

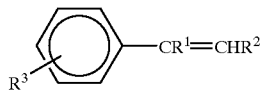

wherein $R^1$, $R^2$, and $R^3$ are all as previously described above. Nonlimiting examples of alkyl substituted styrenes include those selected from the group consisting of 4-nonyl styrene, 4-octyl styrene, 4-(2-ethylhexyl) styrene, 3-octyl styrene, 2-octyl styrene, 4-isobutyl styrene, and mixtures thereof. Also, useful are styrene monomers containing two or more alkyl substituents on the aromatic ring such as 3,5-dimethyl styrene, 2-methyl 4-isopropyl styrene and the like.

Hydrophobic B Macromonomer Units

A macromonomer is a large polymeric type of monomer unit which can be further polymerized with itself, with other conventional monomers, or with other macromonomers. The term "macromonomer" is one that is familiar to the polymer chemist of ordinary skill in the art.

The hydrophobic B macromonomer units of the present invention are large polymeric building blocks containing repeating structural units. The B macromonomers can be formed from the polymerization of smaller monomer units. The B macromonomers encompass a wide variety of structures and are copolymerizable with the A monomer and the optional C polysiloxane macromonomer units. Either a single B macromonomer or combinations of two or more B macromonomers can be utilized, so long as the $T_g$, solubility, and molecular weight requirements of the copolymer are met. Also, each B macromonomer can be constructed from two or more randomly repeating monomer units, in which case the macromonomer would actually be considered a copolymeric type of macromonomer. In any event, the B macromonomers are selected to meet the requirements of the thermoplastic elastomeric copolymers.

The hydrophobic B macromonomers comprise from about 10% to about 60%, more preferably from about 20% to about 55%, and most preferably from about 30% to about 50%, by weight of the copolymers.

By the term "copolymerizable" as used herein is meant B macromonomers that can be reacted with the A monomer and optional C polysiloxane macromonomer in a polymerization reaction using any conventional synthetic techniques. "Copolymerization" is a term of art used to refer to the simultaneous polymerization of two or more different monomers. In the present invention, B macromonomers that are copolymerizable with the A monomers and the optional C polysiloxane macromonomers using conventional free radical initiated techniques are preferred. Without being limited by theory, the hydrophobic B macromonomer units are believed to contribute to the overall solubility properties of the copolymers.

B macromonomers that are useful herein contain a polymeric portion and a copolymerizable moiety, preferably an ethylenically unsaturated moiety that is copolymerizable with the A and optional C units. The term "ethylenically unsaturated" is used herein to mean B macromonomers that contain at least one carbon—carbon double bond (which can be mono-, di-, tri-, or tetra-substituted). Typically, the preferred B macromonomers are those that are endcapped with the ethylenically unsaturated moiety. By "endcapped" as used herein is meant that the ethylenically unsaturated moiety is at or near a terminal position of the macromonomer. However, this definition of "endcapped" is not intended to limit the macromonomer to only those macromonomers which terminate in a carbon—carbon double bond (whether mono-, di-, tri-, or tetra-substituted).

The hydrophobic B macromonomers of the present invention can be synthesized utilizing a variety of standard synthetic procedures familiar to the polymer chemist of ordinary skill in the art. Furthermore, these macromonomers can be synthesized starting from commercially available polymers. Typically the weight average molecular weight of the macromonomer is from about 1000 to about 200,000, more preferably from 1500 to about 30,000, and most preferably from about 2000 to about 25,000.

For example, the hydrophobic B macromonomers can be synthesized by the polymerization (acid, base, free radical, or auto-initiated) of one or more hydrophobic monomers to form a polymer which is subsequently reacted with or "endcapped" with a copolymerizable structural unit E, preferably an ethylenically unsaturated moiety. Alternatively, the B macromonomers can be synthesized starting with commercially available hydrophobic polymers which are "endcapped" with the structural unit E. In yet another alternative, the B macromonomer can be synthesized by starting with the structural unit E, and polymerizing onto it the desired hydrophobic monomer units. It is to be understood that in this third alternative, the ethylenically unsaturated moiety of the E unit is not consumed in the synthesis but its integrity is preserved for subsequent copolymerization of the B macromonomer with the A and optional C units. All of the synthetic alternatives are merely illustrative in that any other suitable synthetic procedures can be utilized to prepare the B macromonomers and copolymers of the present invention.

The B macromonomers can be described by the following formula $$[I]_n-[W]_m-E$$

wherein I is an optionally present initiator (i.e. n=0 or 1), W is a hydrophobic monomer unit, E is an endcapping group, and m is an integer from about 10 to about 2000, preferably from about 15 to about 300, and more preferably from about 20 to about 250, so that the macromonomer meets the weight average molecular weight requirements set forth above.

I is an optionally present chemical initiator moiety. Without being limited by theory, I can be derived from a chemical initiator or solvent used in the synthesis of the B macromonomer. Nonlimiting examples of such initiators from which I can be derived include hydrogen ion, hydrogen radical, hydride ion, hydroxide ion, hydroxyl radical, peroxide radical, peroxide anion, C1–20 carbocations, C1–20 carbanions (e.g., sec-butyl carbanion, and 1,1-diphenyl-4-methylpentyl carbanion), C1–20 carbon radicals, C1–20 aliphatic and aromatic alkoxy anions, ammonium ion, and substituted ammonium ions (e.g., C1–20 alkyl and C1–20 alkoxy substituted). I can be derived from any useful solvent, nonlimiting examples of which include water, methanol ethanol, propanol, isopropanol, acetone, hexane, dichloromethane, chloroform, benzene, and toluene. Nonlimiting examples of I include chemical moieties selected from the group consisting of hydrogen, C1–40 straight or branched chain alkyl, benzyl, 1-phenyl substituted C2–40 straight or branched chain alkyl, 1,1-diphenyl substituted C2–40 straight or branched chain alkyl, and mixtures thereof. More preferably I is selected from the group consisting of 1,1-diphenyl-4-methylpentyl and sec-butyl. Most preferably I is sec-butyl.

W is selected from one or more hydrophobic monomer units, with monomer units corresponding to the following formula being preferred:

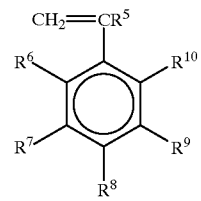

wherein $R^5$ is selected from the group consisting of H and $C_1-C_8$ straight or branched chain alkyl; preferably wherein $R^5$ is selected from the group consisting of H and methyl, more preferably wherein $R^5$ is H. $R^6$, $R^7$, $R^8$, $R^9$, and $R^{10}$ are independently selected from the group consisting of H and C1–C8 straight or branched chain alkyl such that each of $R^6$, $R^7$, $R^8$, $R^9$, and $R^{10}$ are not simultaneously H; preferably $R^6$, $R^7$, $R^8$, $R^9$, and $R^{10}$ are independently selected from the group consisting of H and C1–C4 straight or branched chain alkyl such that each of $R^6$, $R^7$, $R^8$, $R^9$, and $R^{10}$ are not simultaneously H; and more preferably $R^6$, $R^7$, $R^9$, and $R^{10}$ are H and $R^8$ is t-butyl. Nonlimiting examples of hydrophobic monomers useful herein include those selected from the group consisting of 4-t-butyl vinyl benzene, 2,4-dimethyl vinyl benzene, 4-t-butyl methylvinyl benzene (i.e. $R^5$=methyl), 2,4-dimethyl methylvinyl benzene (i.e. $R^5$=methyl), 4-(2-ethylhexyl) vinyl benzene, 4-isopropyl vinyl benzene, 3-methyl vinyl benzene, 4-methyl vinyl benzene, and mixtures thereof. Preferred are monomers selected from the group consisting of 4-t-butyl vinyl benzene, 2,4-dimethyl vinyl benzene, 4-(2-ethylhexyl) vinyl benzene, 4-isopropyl vinyl benzene, 4-methyl vinyl benzene, and mixtures thereof. More preferred are monomers selected from the group consisting of 4-t-butyl vinyl benzene and 2,4-dimethyl vinyl benzene, and mixtures thereof. Additionally, when the B macromonomer is a copolymeric macromonomer, a wide variety of additional monomer units can be utilized in addition to those described in this paragraph, so long as the $T_g$, solubility, and molecular weight requirements of the copolymer are met. Examples of other monomers useful for incorporation into a copolymeric macromonomer include those described previously described above in the description of the A monomer units.

E is a copolymerizable moiety or "endcapping" group. Preferably E is an ethylenically unsaturated moiety. More preferred is when E is selected from the group consisting of vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, cyclohexenyl, cylcopentenyl, and mixtures thereof. Even more preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof. Most preferred is when E is selected from the group consisting of vinyl, allyl, acryloyl, methacryloyl, ethacryloyl, 3-vinylbenzyl, 4-vinylbenzyl, and mixtures thereof.

Alternatively, the B macromonomer can be represented by the alternative formula

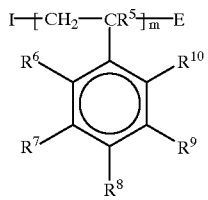

wherein I, E, m, $R^5$, $R^6$, $R^7$, $R^8$, $R^9$, and $R^{10}$ are as previously described herein.

Nonlimiting examples of these endcapped hydrophobic macromonomers include acryloyl endcapped poly(4-t-butyl vinyl benzene), acryloyl endcapped poly(2,4-dimethyl vinyl benzene), 2-, 3-, or 4-vinyl benzyl endcapped poly(4-t-butyl vinyl benzene), 2-, 3-, or 4-vinyl benzyl endcapped poly(2,4-dimethyl vinyl benzene), acryloyl endcapped poly[4-(2-ethylhexyl) vinyl benzene, 2-, 3-, or 4-vinylbenzoyl endcapped poly(4-t-butyl vinyl benzene), 2-, 3-, or 4-vinylbenzoyl endcapped poly(2,4-dimethyl vinyl benzene), and mixtures thereof. More preferred are acryloyl endcapped poly(4-t-butyl vinyl benzene), acryloyl endcapped poly(2,4-dimethyl vinyl benzene), and mixtures thereof. Most preferred is endcapped poly(4-t-butyl vinyl benzene).

Examples of other macromonomers include "copolymer" type B macromonomers containing two or more randomly repeating monomer units. Nonlimiting examples of these "copolymer" type of macromonomers include acryloyl endcapped poly[co(4-t-butyl vinyl benzene)(2,4-dimethyl vinyl benzene)], poly[co(4-t-butyl vinyl benzene)(2-ethylhexyl acrylate)], poly[co(2,4-dimethyl vinyl benzene)(2-ethylhexyl acrylate)], poly[co(2-ethyl vinyl benzene)(octyl methacrylate)], and the like.

The endcapped hydrophobic macromonomers can be synthesized using standard synthetic procedures which involve polymerizing, usually under anionic initiation conditions the appropriate monomer unit, (e.g., 4-t-butyl vinyl benzene, 2,4-dimethyl vinylbenzene, etc.). A wide variety of initiators can be used, nonlimiting examples of which include bases such as n-butyl lithium, sec-butyl lithium, t-butyl lithium, lithium aluminum hydride, sodium hydride, and the like. Nonlimiting examples of these bases are provided in *Anionic Polymerization: Principles and Practice*, Maurice Morton, Chapter 2, p. 13, Academic Press, N.Y. (1983), which is incorporated by reference herein in its entirety. It has been found especially convenient to use these strong bases in conjunction with sterically hindered hydrocarbon materials such as 1,1-diphenyl ethylene to generate a sterically hindered base for initiating the polymerization reaction, in which case, the sterically hindered hydrocarbon is the actual initiator, defined previously as "I", which is incorporated into the macromonomer structure. Once the desired degree of polymerization is achieved, an appropriate endcapping reagent is typically used to terminate the polymerization and to endcap the macromonomer. Nonlimiting examples of these endcapping reagents include 2-vinylbenzyl chloride, 3-vinylbenzyl chloride, 4-vinylbenzyl chloride, and the like. Alternatively, the endcapping can be achieved by reacting the polymeric reaction mixture with one equivalent of ethylene oxide to terminate the polymer with a —$CH_2CH_2$—O— moiety, followed by reaction with an endcapping reagent such as an unsaturated acid halide.

Polysiloxane C Macromonomer Units

The optional polysiloxane C macromonomer units are large monomer building blocks containing a polysiloxane portion (i.e. a polysiloxane chain) and a moiety copolymerizable with said A and B units. A polysiloxane is a polymer containing repeating silicon-oxygen bonds.

The polysiloxane C monomer units comprise from 0% to about 20%, more preferably from 0% to about 15%, and most preferably from 0% to about 10%, by weight of the copolymers.

By the term "copolymerizable" as used herein is meant C polysiloxane macromonomer units that can be reacted with the A monomer and the B macromonomer in a polymerization reaction using any conventional synthetic techniques. The C polysiloxane macromonomer units that are useful herein contain a copolymerizable moiety, preferably an ethylenically unsaturated moiety, that is copolymerizable with the A and B units. The term "ethylenically unsaturated" is used herein to mean C polysiloxane units that contain at least one carbon—carbon double bond (which can be mono-, di-, tri-, or tetra-substituted). Typically, the preferred C polysiloxanes are those that are endcapped with the ethylenically unsaturated moiety. By "endcapped" as used herein is meant that the ethylenically unsaturated moiety is at or near a terminal position of the macromonomer.

However, this definition of "endcapped" is not intended to limit the macromonomer to only those macromonomers which terminate in a carbon—carbon double bond (whether mono-, di-, tri-, or tetra-substituted).

Examples of polysiloxane macromonomer units which are useful as the polysiloxane C units herein are described in U.S. Pat. No. 5,106,609, to R. E. Bolich, Jr. et al., issued Apr. 21, 1992; and U.S. Pat. No. 4,693,935, to Mazurek, issued Sep. 15, 1987, which are both incorporated by reference herein in their entirety.

Either a single C polysiloxane macromonomer or combinations or two or more C polysiloxane macromonomers can be utilized. In either case, the polysiloxane macromonomers are selected to meet the requirements of the copolymer.

The C polysiloxane units can be described by the following formula

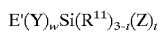

wherein E' is an ethylenically unsaturated moiety or "endcapping" group copolymerizable with A and B; Y is a divalent linking atom or group of atoms; $R^{11}$ is selected from the group consisting of H, lower alkyl, aryl, or alkoxy; Z is a monovalent siloxane polymeric moiety having a number average molecular weight of at least about 500, is essentially unreactive under copolymerization conditions, and is pendant from said backbone after polymerization; w is 0 or 1; and t is an integer from 1 to 3.

The C unit has a weight average molecular weight of from about 1000 to about 50,000, preferably from about 5000 to about 40,000, more preferably from about 10,000 to about 20,000.

Preferred C polysiloxane units are those selected from the group consisting of

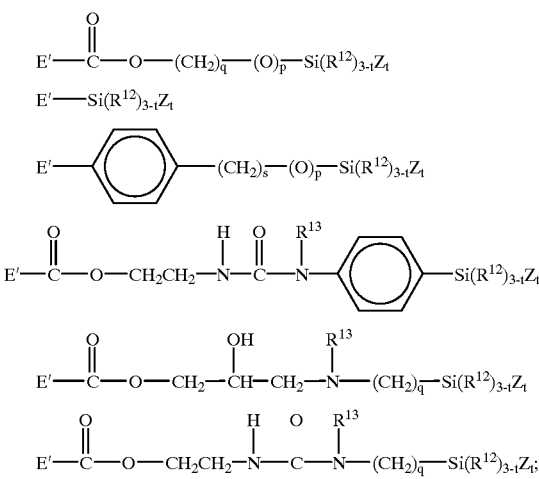

wherein t is 1, 2, or 3, preferably t is 1; p is 0 or 1, preferably p is 0; $R^{13}$ is alkyl or hydrogen; q is an integer from 2 to 6, preferably q is 3; s is an integer from 0 to 2; E' is represented by the structure

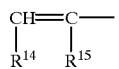

wherein $R^{14}$ is hydrogen or —COOH, preferably $R^{14}$ is hydrogen; $R^{15}$ is hydrogen, methyl or —CH$_2$COOH, preferably $R^{15}$ is methyl; Z is

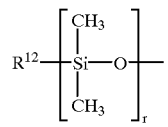

wherein $R^{12}$ is alkyl, alkoxy, alkylamino, aryl, or hydroxyl preferably $R^{12}$ is alkyl); and r is an integer from about 5 to about 700, preferably r is about 250.

Polymers of the Present Invention

Particularly preferred polymers for use in the present invention include the following (the weight percents below refer to the amount of reactants added in the polymerization reaction, not necessarily the amount in the finished polymer):

n-butyl acrylate/poly(4-t-butyl vinyl benzene) 70/30 n-butyl acrylate/2-ethylhexyl acrylate/poly(4-t-butyl vinyl benzene) 40/20/30 n-butyl acrylate/2-ethylhexyl acrylate/poly(4-t-butyl vinylbenzene)/poly(dimethylsiloxane) 36/22/40/2 n-butyl acrylate/poly(2,4-dimethyl vinyl benzene) 60/40 n-butyl acrylate/2-ethylhexyl acrylate/poly(2,4-dimethyl vinyl benzene) 40/20/40 n-butyl acrylate/2-ethylhexyl acrylate/poly(2,4-dimethyl vinylbenzene)/poly(dimethylsiloxane) 36/22/40/2 n-butyl acrylate/2-methoxyethyl acrylate/poly(4-t-butyl vinylbenzene)/poly(dimethylsiloxane) 36/22/40/2 n-butyl acrylate/2-methoxyethyl acrylate/poly(4-t-butyl vinylbenzene)/poly(dimethylsiloxane) 33/22/40/5 n-butyl acrylate/2-methoxyethyl acrylate/poly(4-t-butyl vinylbenzene) 38/22/40 n-butyl acrylate/2-methoxyethyl acrylate/poly(4-t-butyl vinylbenzene) 50/20/30

Synthesis of the Copolymers

The copolymers can be made by free radical polymerization of the A monomers with the B macromonomers and the optional C polysiloxane macromonomers. It is not intended to necessarily exclude from this invention any copolymers made by means other than free radical polymerization, so long as the product has the desired physical properties. The copolymers herein are formed from randomly repeating A monomer units, B macromonomer units, and C polysiloxane macromonomer units.

The general principles of free radical polymerization methods are well understood. See, for example, Odian, "Principles of Polymerization", 2nd edition, John Wiley & Sons, 1981, pp. 179–318. The desired monomers and macromonomers are all placed in a reactor, along with a sufficient amount of a mutual solvent so that when the reaction is complete the viscosity of the reaction is reasonable. Typical monomer and macromonomer loadings are from about 10% to about 50%, on a weight basis. Undesired terminators, especially oxygen, can be removed as needed. This is done by evacuation or by purging with an inert gas, such as argon or nitrogen. The initiator is introduced and the reaction brought to the temperature needed for initiation to occur, assuming thermal initiators are used. Nonlimiting examples of suitable initiators include those selected from the group consisting of azo initiators, peroxide initiators, redox initiators, and photochemical initiators. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as needed utilizing a variety of techniques including filtration, extraction, trituration, membrane separation, gel permeation chromatography, and like.

There are numerous variations on these procedures which are entirely up to the discretion of the synthetic chemist (e.g., choice of degassing method and gas, choice of initiator type, extent of conversion, reaction loading, etc.). The choice of initiator and solvent are often determined by the requirements of the particular monomers and macromonomer used, because different monomers and macromonomers have different solubilities and different reactivities to a specific initiator.

The copolymers of the present invention can also be synthesized by first preparing the backbone and optional polysiloxane side chains from the copolymerization of suitable monomers and polysiloxane macromonomers, followed by further polymerization of the resulting intermediary copolymer with suitable hydrophobic monomers to form the hydrophobic side chains. In yet other alternatives, the optional polysiloxane side chains can be added by polymerizing silicon-containing moieties onto an intermediate copolymer prepared from suitable monomers and hydrophobic macromonomers.

Analysis of the copolymer reaction product and the extracted materials, and the purified copolymer can be performed by conventional analysis techniques known in the art. These include, for example, nuclear magnetic resource (NMR), infrared molecular spectroscopies, gel permeation/size exclusion chromatography, membrane osmometry, and atomic absorption and emission spectroscopies.

Water Insoluble Solvent for the Thermoplastic Elastomeric Copolymers

The compositions of the present invention comprise a water insoluble volatile liquid which is a solvent for the copolymers of the present invention.

In general, the present compositions will comprise from about 0.1% to about 50%, preferably from about 0.2% to about 25%, and more preferably from about 0.5% to about 15%, by weight of the total composition, of the solvent.

As used herein, the term "volatile" refers to liquids having a boiling point at one atmosphere of 260° C. or less, preferably 250° C. or less, more preferably 230° C. or less, most preferably 225° C. or less. In general, the boiling point of the volatile solvents will be at least about 50° C., preferably at least about 100° C. The term "nonvolatile", on the other hand, shall refer to materials which have a boiling point at one atmosphere of greater than 260° C. "Water insoluble solvent" refers to a solvent that is not miscible with water (distilled or equivalent) at 25° C.

The solvents hereof include silicone fluids, silane fluids, and organic oils such as hydrocarbons, esters, ethers, alcohols, and mixtures thereof.

Especially preferred are volatile silicone fluids. Volatile silicone fluids suitable for use herein include both linear and cyclic silicone fluids. The viscosity of the volatile silicone fluids hereof will generally be about 10 cS or less at 25° C.

Volatile silicone fluids include polyalkylsiloxanes, polyalkylarylsiloxanes, and mixtures thereof.

Cyclic volatile silicone fluids include cyclopolysiloxanes such as cycloalkylsiloxanes and cycloalkylalkoxysiloxanes, wherein alkyl and alkoxy groups contain $C_1$–$C_8$ alkyl groups.

A general formula for cyclic volatile silicones contemplated for use herein is:

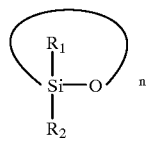

wherein n=3–7 and $R_1$ and $R_2$ are independently selected from $C_1$–$C_8$ alkyl, aryl (especially phenyl), and alkaryl (e.g., $C_1$–$C_8$ substituted aryl). Preferred are $R_1$ and $R_2$ being $C_1$–$C_2$ alkyl, most preferably $C_1$ and n=4–6. $R_1$ and $R_2$ can also be alkoxy, alkaryl, hydroxy, hydroxyalkyl, and derivatives thereof.

Specific examples of solvents include octomethyl cyclotetrasiloxane, decamethyl cyclopentasiloxane, methoxypropyl heptamethyl cyclotetrasiloxane, octomethyl cyclotetrasiloxane, and decamethyl cyclopentasiloxane. The volatile silicone solvents are cyclic and linear polydimethylsiloxane. The number of silicone atoms in the preferred cyclic silicones is from about 3 to about 7, more preferably 4 or 5.

Linear volatile silicone fluids include polyorganosiloxanes such as polydialkylsiloxanes, polyalkylarylsiloxanes.

Examples of linear polyorganosiloxanes include those having from about 3 to about 9 silicon atoms are represented by the general formula:

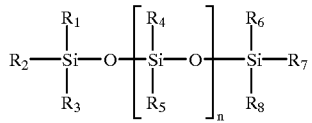

wherein $R_1$, $R_2$, $R_3$, $R_4$, $R_5$, $R_6$, $R_7$, and $R_8$ can independently be saturated or unsaturated $C_1$–$C_8$ alkyl, aryl, (preferably containing a $C_6$ aromatic ring), alkyl aryl, hydroxyalkyl, amino alkyl or alkyl siloxy, and n=1–7. The preferred volatile linear polydimethylsiloxanes have from about 3 to 9 silicone atoms and are polydialkylsiloxanes, especially those with $C_1$–$C_2$, preferably $C_1$, alkyls.

Examples of preferred linear materials include polydialkylsiloxanes such as polydimethylsiloxanes having a viscosity below about 10 cS at 25° C., and disiloxanes such as phenylpentamethyldisiloxane, chloropropyl pentamethyldisiloxane, and hydroxypropylpentamethyldisiloxane.

The linear volatile silicones generally have viscosities of 5 centistokes or less at 25° C., while the volatile cyclic materials generally have viscosities of 10 centistokes or less at 25° C. A description of volatile silicones is found in Todd and Byers, "Volatile Silicone Fluids for Cosmetics", *Cosmetics and Toiletries*, Vol. 91, January, 1976, pp. 27–32, incorporated herein by reference.

Volatile silane liquids can also be used. Suitable silane compounds include those that have the general formula:

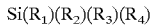

wherein $R_1$, $R_2$, $R_3$ and $R_4$ can independently be selected from $C_1$–$C_8$ alkyl, aryl, alkyl aryl, hydroxy alkyl and alkylsiloxy.

Other volatile solvents useful in the present compositions include hydrocarbons, esters, ethers, alkyl alcohols, and mixtures thereof. Preferred of these are the ester, ether, alkyl alcohol, and hydrocarbon fluids.

The hydrocarbons may be either straight or branched chain and may contain from about 10 to about 16, preferably from about 12 to about 16 carbon atoms. Examples of suitable straight chain hydrocarbons are decane, dodecane, decene, tridecane and mixtures thereof. Suitable branched chain hydrocarbon solvents include $C_{10}$–$C_{16}$ branched chain hydrocarbons, and mixtures thereof, preferably $C_{11}$–$C_{14}$ branched chain hydrocarbons, more preferably $C_{12}$ branched chain hydrocarbons. Saturated hydrocarbons are preferred, although it isn't necessarily intended to exclude unsaturated hydrocarbons. Examples of such branched chain hydrocarbons include isoparaffins of the above chain sizes. Isoparaffins are commercially available from Exxon Chemical Co. Examples include Isopar™ H and K ($C_{11}$–$C_{12}$ isoparaffins), and Isopar™ L ($C_{11}$–$C_{13}$ isoparaffins). Another suitable branched chain hydrocarbon is isododecane. Isododecane is commercially available from Preperse, Inc. (South Plainfiled, N.J., USA) as Permethyl™ 99A. Also contemplated, though not preferred, are the terpenes such as orange and lemon terpenes.

Useful alkyl alcohols will typically contain from about 8 to about 12 carbon atoms and can be saturated or unsaturated, and have branched or straight chains. Suitable alkyl alcohols include, for example, linalool and decyl alcohol.

Useful esters include, for example, methyl alkanoates such as the $C_8$–$C_{12}$ alkanoates (e.g., methyl decanoate), di($C_2$–$C_3$)alkyl adipates (e.g., diethyl adipate, diisopropyl adipate), $C_6$–$C_{10}$ alkyl acetates (e.g., octyl acetate), and benzoates (e.g., butyl benzoate).

Useful ethers include di($C_5$–$C_7$) alkyl ethers, especially the di($C_5$–$C_6$) alkyl ethers such as dipentyl ether and dihexyl ether.

The preferred volatile solvents hereof are the silicone fluids, especially the cyclic silicone fluids, and $C_{10}$–$C_{16}$ branched chain hydrocarbons.

Hair Care Compositions

The compositions of the present invention also comprise a suitable carrier or hair care matrix for delivering the copolymer and the water insoluble volatile solvent to the hair. Any carrier suitable for delivery of the copolymer/volatile solvent to the hair can be used. The carrier can comprise a volatile liquid which is water or is otherwise water soluble, or a mixture thereof and in which the volatile solvent of the polysiloxane-grafted polymer is not be soluble. In general, the compositions will comprise from about 50% to about 99.3%, preferably from about 70% to about 99%, more preferably from about 85% to about 98%, of carrier or hair care matrix.

The carrier liquid herein can include water and other hydrophilic fluids, and combinations thereof. Suitable carrier fluids for use in the present invention, in addition to water, include lower alcohols ($C_1$–$C_4$ alcohols, preferably $C_2$–$C_4$ alcohols such as ethanol and isopropanol) and mixtures of lower alcohols. Preferred solvents include water, ethanol, and mixtures thereof. Especially preferred is water.

The preferred compositions are in the form of a discontinuous phase of dispersed droplets, or particles, of the thermoplastic elastomeric copolymer and the water insoluble volatile solvent distributed throughout the carrier. The carrier can also comprise a variety of other components, such as other active ingredients, rheology modifiers such as thickeners, gelling agents, etc. The compositions of the present invention can be in the form of liquids, lotions, creams gels, etc.

The carrier may include gel vehicle materials or other rheology modifiers. These are particularly contemplated for use in products such as hair rinses, shampoos, mousses, and creams and lotions.

Gel vehicles can comprise two essential components: a lipid vehicle material and a cationic surfactant vehicle material. Cationic surfactant materials are described in detail below. Gel vehicles are generally described in the following documents, all incorporated by reference herein: Barry, "The Self-Bodying Action of the Mixed Emulsifier Sodium Dodecyl Sulfate/Cetyl Alcohol", 28 J. of Colloid and Interface Science 82–91 (1968); Barry, et al., "The Self-Bodying Action of Alkyltrimethylammonium Bromides/Cetostearyl Alcohol Mixed Emulsifiers; Influence of Quaternary Chain Length", 35 J. of Colloid and Interface Science 689–708 (1971); and Barry, et al., "Rheology of Systems Containing Cetomacrogol 1000-Cetostearyl Alcohol, I. Self Bodying Action", 38 J. of Colloid and Interface Science 616–625 (1972).

The carrier may incorporate one or more lipid vehicle materials, regardless of whether it also contains a cationic surfactant, which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Lipid vehicle materials among those useful herein are disclosed in *Bailey's Industrial Oil and Fat Products*, (3rd edition, D. Swern, ed., 1979), incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fuku Shima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is typically present at from about 0.1% to about 10.0% of the composition; the cationic surfactant vehicle material is present at from about 0.05% to about 5.0% of the composition.

The use of nonionic cellulose ethers and water-soluble gums for thickening compositions are also contemplated. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum, each incorporated herein by reference.

Cellulose ethers are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

Nonionic water-soluble cellulose ethers are preferred polymers that can be employed in hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Other carrier ingredients for use in the compositions of the present invention, especially for hair rinses, include combinations of hydrophobically-modified polymeric materials with surfactants, such as quaternary ammonium compounds (such as ditallowdimethyl ammonium chloride). These vehicles are described in detail in the following patents: U.S. Pat. No. 5,106,609, issued Apr. 21, 1992 to Bolich et al., U.S. Pat. No. 5,100,658, issued Mar. 31, 1992 to Bolich et al., U.S. Pat. No. 5,104,646, issued Apr. 14, 1992 to Bolich et al., and U.S. Pat. No. 5,100,657, issued Mar. 31, 1992 to Ansher-Jackson et al., each incorporated herein by reference.

It is also contemplated to utilize a suspending agent to thicken the compositions and/or suspend the polymer/resin/solvent phase. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_8$–$C_{22}$ (preferably $C_{12}$–$C_{22}$, more preferably $C_{16}$–$C_{18}$) amido benzoic acid, or soluble salt (e.g., K, Na salts) thereof particularly N,N-di(hydrogenated)tallow amido benzoic acid which is commercially marketed by Stepan Company (Northfield, Ill., USA).

These systems provide a gel-like rheology without necessarily being gels in the technical sense. By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

Nonionic water-soluble cellulose ethers are preferred to be employed as the polymer substrate of these hydrophobically modified polymers. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The long chain alkyl modifier can be attached to the cellulose ether substrate via an ether, ester or urethane linkage. The ether linkage is preferred.

One commercially available material which meets these requirements is NATROSOL PLUS Grade 430, hydrophobically modified hydroxyethylcellulose available from Aqualon Company, Wilmington, Del. This material has a $C_{16}$ alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

Another material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

Examples of water soluble polymers include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone, dextrans, for example Dextran purified crude Grade 2P, available from D&O Chemicals, plant exudates such as acacia, ghatti, and tragacanth, seaweed extracts such as sodium alginate, propylene glycol alginate, sodium carrageenan, cationic polymers such as Ucare JR-polymer (a cationic modified hydroxyethyl cellulose available from Union Carbide), natural polysaccharide materials, such as guar gum, locust bean gum, and xanthan gum.

When such systems are used to thicken the present compositions, from about 0.3% to about 5.0%, preferably from about 0.4% to about 3.0%, of the hydrophobically modified nonionic polymer is preferably utilized with from about 0.3% to about 5.0%, preferably from about 0.4% to about 3.0%, of the water-soluble polymeric material.

An alternative secondary thickening material for the hydrophobically modified nonionic polymer is a water-soluble surfactant having a molecular weight of less than about 20,000. By "water-soluble surfactant" is meant surfactant materials which form substantially clear, isotropic solutions when dissolved in water at 0.2 weight percent at 25° C.

Essentially any water-soluble surfactant material which meets these requirements will work in the present invention. However, the following materials have been found to be particularly preferred: cetyl betaine, ammonium lauryl sulfate, ammonium laureth sulfate, cetyl trimethyl ammonium chloride, and mixtures thereof.

When such systems are used to thicken the present compositions, from about 0.1% to about 10.0%, preferably from about 0.2% to about 5.0%, of the hydrophobically-modified nonionic water soluble polymer is generally utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

When the hydrophobically-modified polymer is combined with is a water-insoluble surfactant having a molecular weight of less than about 20,000. By "water-insoluble surfactant" is meant surfactant materials which do not form substantially clear isotropic solutions when dissolved in water at greater than 0.2 weight percent at 25° C.

Essentially any water-insoluble surfactant material which meets these requirements will work in the present invention, however, water-insoluble cationic surfactant materials are preferred. Cationic surfactants are described below. The following nonexclusive materials are suitable: stearamide diethanolamine (stearamide DEA), cocoamide methanolamine (cocoamide MEA), dimethyl stearamine oxide, glyceryl monooleate, sucrose stearate, PEG-2 stearamine, polyethylene glycol ethers of fatty alcohols, such as Cetheth-2 of the formula $CH_3-(CH2)14-CH2-(OCH2CH2)_n-OH$, where n has an average value of 2 (commercially available under the trade name Brij 56 from ICI Americas), glycerol stearate citrate, dihydrogenated tallow dimethyl ammonium chloride, polyoxyethylene, polyoxypropylene block polymers such as Poloxamer 181, of the formula:

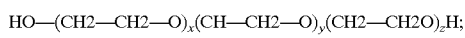

wherein on average x=3, y=30 and z=3 (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0%, of the hydrophobically-modified hydroxyethyl cellulose is generally utilized with from about 0.02% to about 10.0%, preferably from about 0.05% to about 3.0%, most preferably from about 0.05% to about 2.0%, of the water-insoluble surfactant.

Cationic surfactants useful in the compositions of the present invention, including the gel vehicle systems as well as hydrophobically modified cellulose vehicle systems, contain amino or quaternary ammonium hydrophilic moieties which are positively charged when dissolved in the aqueous composition of the present invention. Cationic surfactants among those useful herein are disclosed in the following documents, all.

Surfactants

Surfactants are optional ingredients in the compositions of the invention, particularly shampoo and conditioner compositions. When present, the surfactant typically comprises from about 0.05% to about 50% of the composition. For a shampoo, the level is preferably from about 10% to about 30%, most preferably from about 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants.

Synthetic anionic detergents useful herein, particularly for shampoo compositions, include alkyl and alkyl ether sulfates. These materials typically have the respective formulae $ROSO_3M$ and $RO(C_2H_4O)_xSO_3M$, wherein R is alkyl or alkenyl of from about 10 to about 20 carbon atoms, x is 1 to 10, and M is a water-soluble cation such as ammonium, sodium, potassium and triethanolamine.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuc cinicacid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The α-olefins from which the olefin sulfonates are derived are mono-olefins having about 12 to about 24 carbon atoms, preferably about 14 to about 16 carbon atoms. Another class of anionic organic surfactants are the β-alkyloxy alkane sulfonates. These compounds have the following formula:

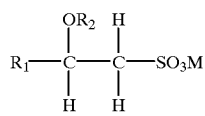

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional nonsoap synthetic anionic surfactants are described in *McCutcheon's, Detergents and Emulsifiers,* 1984 *Annual*, published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. Those derived from the condensation of ethylene oxide with the product resulting from the reaction of propylene oxide and ethylene diamine products.

2. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

3. Long chain tertiary amine oxides such as those corresponding to the following general formula:

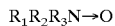

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals (the arrow in the formula is a conventional representation of a semipolar bond).

4. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond.

5. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetra decyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

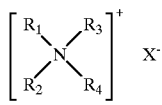

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated.

Other quaternary ammonium salts useful herein are diquaternary ammonium salts, such as tallow propane diammonium dichloride.

Quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieocosyol dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(saturated or unsaturated tallow) dimethyl ammonium chloride is a particularly preferred quaternary ammonium salt.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Zwitterionic surfactants, useful in shampoos as well as conditioners, are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

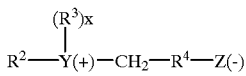

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alpha carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylamino propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Silicone Hair Conditioning Agent

An optional component of the present invention is a nonvolatile, silicone conditioning agent which is not intermixed in the same phase as the volatile solvent of the polysiloxane-grafted copolymer.

The silicone hair conditioning agent for use herein will preferably have an average viscosity of from about 1,000 to about 2,000,000 centistokes at 25° C., more preferably from about 10,000 to about 1,800,000, even more preferably from about 100,000 to about 1,500,000. The viscosity of silicones herein can, in general, be measured by means of a glass capillary viscometer as set forth in Dow Coming Corporate Test Method CTM0004, Jul. 20, 1970.

The silicone hair conditioning agent will typically be used in the shampoo compositions hereof at levels of from about 0.05% to about 10% by weight of the composition, preferably from about 0.1% to about 10%, more preferably from about 0.5% to about 8%, most preferably from about 0.5% to about 5%.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

Silicone fluids hereof also include polyalkyl or polyaryl siloxanes with the following structure:

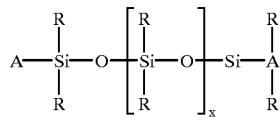

wherein R is alkyl or aryl, and x is an integer from about 1 to about 8,000 may be used, preferably from about 5 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their Viscasil$^R$ and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Coming as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Cationic Polymer Hair Conditioning Agent

The compositions of the present invention can also comprise a water soluble, cationic organic polymer conditioning agent for hair. The polymeric cationic conditioning agent hereof will generally be present at levels of from about 0.05% to about 5%, preferably from about 0.1% to about 4%, more preferably from about 0.2% to about 3%, by weight, of the shampoo composition. By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The cationic organic polymers useful in the hair conditioning agent hereof are organic polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

The cationic charge density is preferably at least about 0.9 meq/gram, more preferably at least about 1.0 meq/gram, even more preferably at least abut 1.1 meq/gram, most preferably at least about 1.2 meq/gram. The cationic charge density is preferably no greater than about 4 meq/gram, more preferably no greater than about 3.0 meq/gram, most preferably no greater than about 2.0 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use, which will in general be from about pH 3 to about pH 9, most generally from about pH 4 to about pH 8.

Any anionic counterions can be utilized for the cationic polymers so long as the water solubility criteria is met.

Suitable counterions include halides (e.g., Cl—, Br—, I—, or F—, preferably Cl—, Br—, or I—), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyidiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

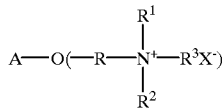

wherein:

A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer $JR^R$ and $LR^R$ series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their $Jaguar^R$ series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

Organic Oil Conditioning Agents

The compositions of the present invention can also comprise a nonvolatile, water insoluble, organic, oil as a conditioning agent for hair. The hair conditioning oily liquid can add shine and luster to the hair. The conditioning oil is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

By "water insoluble" what is meant is that the oily liquid is not soluble in water (distilled or equivalent) at a concentration of 0.1%, at 25° C.

The conditioning oil hereof generally will have a viscosity of about 3 million cs or less, preferably about 2 million cs or less, more preferably about 1.5 million cs or less.

The conditioning oils hereof are liquids selected from the group consisting of hydrocarbon oils and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms, although it is not necessarily meant to be limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350. Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, sold by Permethyl Corporation. A preferred hydrocarbon polymer is polybutene, such as the copolymer of isobutylene and butene. A commercially available material of this type is L-14 polybutene from Amoco Chemical Co. (Chicago, Ill., U.S.A).

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearyol stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

The compositions herein can contain a variety of other optional components suitable for rendering such compositions more cosmetically or aesthetically acceptable or to provide them with additional usage benefits, e.g. medicinal benefits. Such conventional optional ingredients are well-known to those skilled in the art, e.g., sunscreens, medicaments (e.g. anti-bacterials, anti-inflamatories, anti-acne actives, etc.), colors and dyes, perfumes, pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin, disobutyl adipate, butyl stearate, and propylene glycol. Such optional ingredients generally are used individually at levels of from about 0.01% to about 10.0%, preferably from about 0.05% to about 5.0%, of the composition.

The pH of the present compositions generally will be between about 3 and about 9, preferably between about 4 and about 8.

As with all compositions, the present invention should not contain components which unduly interfere with the performance of the compositions.

The hair care compositions of the present invention can be made using conventional formulation and mixing techniques. Methods of making various types of cosmetic compositions are described more specifically in the following examples.

Method of Using Hair Care Compositions

The hair care compositions of the present invention are used in conventional ways to provide the desired benefit appropriate to the product such as hair styling, holding, cleansing, conditioning and the like for hair care compositions. Such methods of use depend upon the type of composition employed but generally involve application of an effective amount of the product to the hair, which may then be rinsed from the hair (as in the case of shampoos and some conditioning products) or allowed to remain on the hair (as in the case of spray, mousse, or gel products). By "effective amount" is meant an amount sufficient to provide the benefit desired. Preferably, hair rinse, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

Acryloyl Endcapped Poly(4-t-butyl Vinyl Benzene) Macromonomer

Approximately 800 mL of dry tetrahydrofuran is placed in a round bottom flask equipped with a mechanical stirrer and a thermometer and is cooled to −78° C. using a dry ice/isopropanol bath. Next, 7.69 ml (0.01 mole) of sec-butyl lithium (1.3 Molar solution in hexane) is added. The mixture is then allowed to stir for 5 minutes. Next, 100.00 gram (0.624 mole) of 4-t-butyl vinyl benzene is added dropwise with stirring. After the addition is complete, ethylene oxide is bubbled into the reaction mixture, which is allowed to stir for 5 minutes. Next, 1.36 grams (0.015 mole) of acryloyl chloride is added, and the reaction mixture is allowed to warm to room temperature with stirring. The reaction mixture is next allowed to warm to room temperature with stirring. The reaction product is then rotary evaporated to yield 95 grams (95% yield) of the macromonomer.

Example 2

Methacryloyl Endcapped Poly(2,4-dimethyl Vinyl Benzene) Macromonomer

Approximately 800 mL of dry tetrahydrofuran is placed in a round bottom flask equipped with a mechanical stirrer and a thermometer and is cooled to −78° C. using a dry ice/isopropanol bath. Next, 7.69 ml (0.01 mole) of sec-butyl lithium (1.3 Molar solution in hexane) and 1.89 grams (0.0124 mole) of diphenylethylene are added. The mixture is then allowed to stir for 5 minutes. Next, 100 grams (0.756 mole) of 2,4-dimethyl vinyl benzene is added dropwise with stirring. Next, 1.60 grams (0.015 mole) of methacryloyl chloride is added, and the reaction mixture is allowed to warm to room temperature with stirring. The reaction product is then rotary evaporated to yield 95 grams (95% yield) of the macromonomer.

Example 3

Using the methods of Examples 1 and 2, a wide variety of macromonomers are prepared by varying the reaction components. Nonlimiting examples of other monomers which can be used to replace the 4-t-butyl vinyl benzene and/or the 2,4-dimethyl vinyl benzene include 4-isopropyl vinyl benzene, 4-(2-ethylhexyl) vinyl benzene, 3-ethyl vinyl benzene, 1-methyl 1-(4-methylphenyl) ethene, and 1-ethyl 1-(4-t-butylphenyl) ethene. Nonlimiting examples of other endcapping reagents which can be used to replace the acryloyl chloride and/or the methacryloyl chloride include 4-vinyl benzoyl chloride, 3-vinyl benzoyl chloride, acryloyl bromide, and 2-ethyl 2-propenoic acid chloride.

Example 4

Synthesis of Poly(n-butyl Acrylate)-graft-poly(4-t-butyl Vinyl Benzene) Thermoplastic Elastomeric Copolymer This polymer can be designated as having the following weight percentages of monomers and macromonomers: n-butyl acrylate/poly(4-t-butyl vinyl benzene) 80/20.

To a solution of 16.0 grams (0.0128 mole) of n-butyl acrylate, and 4 grams of acryloyl endcapped poly(4-t-butyl vinyl benzene)macromonomer from Example 1 in 100 mL of acetone is added 0.03 grams (0.00018 mol) of azoisobutryonitire (AIBN) initiator. The resulting solution is refluxed slowly for about 20 hours. The reaction is then quenched by the addition of about 5 mL of methanol. The solution is then poured into a teflon pand and the acetone is evaporated at room temperature under a fume hood. The resulting polymer film is redissolved in ethanol, filtered, and the ethanol is then evaporated to yield about 18.4 grams of the thermoplastic elastomeric copolymer.

Alternatively, by varying the monomers and macromonomers used, this general procedure is used to prepare other copolymers of the present invention.

Example 5

Synthesis of Poly(n-butyl Acrylate co 2-ethylhexyl Acrylate)-graft-poly(4-t-butyl Vinyl Benzene) Thermoplastic Elastomeric Copolymer This polymer can be designated as having the following weight percentages of monomers and macromonomers: n-butyl acrylate/2-ethylhexyl acrylate/poly(4-t-butyl vinyl benzene) 45/25/30.

To a solution of 7.0 grams (0.07 mole) of n-butyl acrylate, 5.0 grams (0.0274 mole) of 2-ethylhexyl acrylate and 6.0 grams of acryloyl endcapped poly(4-t-butyl vinyl benzene) macromonomer from Example 1 in 40 mL of tetrahydrofuran is added 0.03 grams (0.00018 mole) of AIBN initiator. The resulting solution is refluxed slowly for about 20 hours. The reaction is then quenched by the addition of about 5 mL of methanol. The solution is then poured into a teflon pan and the tetrahydrofuran is evaporated at room temperature under a fume hood. The resulting polymer film is redissovied in tetrahydrofuran, filtered, and the tetrahydrofuran is then evaporated to yield about 18.0 grams of the thermoplastic elastomeric copolymer.

Alternatively, by varying the monomers and macromonomers used, this general procedure is used to prepare other copolymers of the present invention.

Example 6

Synthesis of Poly(n-butyl Acrylate)-graft-[poly(4-t-butyl Vinyl Benzene):Polydimethylsiloxane)]

This polymer can be designated as having the following weight percentages of monomers and macromonomers: n-butyl acrylate/poly(4-t-butyl vinyl benzene)/polydimethylsiloxane 58/40/2.

To a solution of 5.8 grams (0.0453 mole) of n-butyl acrylate, 0.20 grams (0.00002 mole) of poly(dimethylsiloxane) macromonomer (10,000 MW, commercially available from Chisso Corp., Tokyo, Japan) and 4.0 grams (0.0004 mole) of poly(4-t-butyl vinyl benzene) macromonomer (from Example 2) in 90 mL of tetrahydrofuran is added 0.015 grams (0.0001 mole) of AIBN initiator. The resulting solution is refluxed for about 24 hours. The reaction is then quenched by the addition of about 5 mL of methanol. The solution is then poured into a teflon pan and the tetrahydrofuran is evaporated at room temperature under a fume hood. The resulting polymer film is redissolved in tetrahydrofuran, filtered, and the tetrahydrofuran is then evaporated to yield about 9.0 grams of the copolymer.

Alternatively, by varying the monomers and macromonomers used, this general procedure is used to prepare other copolymers of the present invention.

Example 7

Synthesis of Poly[(n-butyl Acrylate)-co-2-ethylhexyl Acrylate]graft-[poly(4-t-butyl Vinyl Benzene):Polydimethylsiloxane)]

This polymer can be designated as having the following weight percentages of monomers and macromonomers: n-butyl acrylate/2-ethylhexyl acrylate/poly(4-t-butyl vinyl benzene)/polydimethylsiloxane 36/22/40/2.

To a solution of 3.60 grams (0.0281 mole) of n-butyl acrylate, 2.20 grams (0.012 mole) of 2-ethylhexyl acrylate, 0.20 grams (0.00002 mole) of poly(dimethylsiloxane) macromonomer (10,000 MW, commercially available from Chisso Corp., Tokyo, Japan) and 4.0 grams (0.0004 mole) of poly(4-t-butyl vinyl benzene) macromonomer (from Example 2) in 90 mL of tetrahydrofuran is added 0.015 grams (0.0001 mole) of AIBN initiator. The resulting solution is refluxed for about 24 hours. The reaction is then quenched by the addition of about 5 mL of methanol. The solution is then poured into a teflon pan and the solvent is evaporated at room temperature under a fume hood. The resulting polymer film is redissolved in tetrahydrofuran, filtered, and the tetrahydrofuran is then evaporated to yield about 9.0 grams of the copolymer.

Alternatively, by varying the monomers and macromonomers used, this general procedure is used to prepare other copolymers of the present invention.

Examples 8–10

The following are hair styling/conditioning rinse compositions representative of the present invention.

| Composition | 8 | 9 | 10 |
|---|---|---|---|
| Conditioner Premix | | | |
| Water | q.s. | q.s. | q.s. |
| Citric Acid | 0.02 | 0.02 | 0.02 |
| Sodium Citrate | 0.09 | 0.09 | 0.10 |
| Cetyl Alcohol | 0.12 | 0.12 | 0.12 |
| Stearyl Alcohol | 0.08 | 0.08 | 0.08 |
| Natrosol Plus CS Grade D-67[1] | 1.02 | 1.00 | 0.99 |
| Xanthan Gum[2] | 0.25 | 0.25 | 0.25 |
| Styling Polymer Premix | | | |
| Polymer in Example 7 | 1.75 | 1.75 | 1.75 |
| Permethyl 99A | 8.54 | 8.54 | 8.54 |
| Trimethylsiloxysilicate | 0.11 | 0.11 | 0.11 |
| Kathon CG | 0.03 | 0.03 | 0.03 |
| Perfume | 0.33 | 0.33 | 0.33 |
| Silicone Premix | | | |
| DRO Water | 9.48 | 9.48 | 8.57 |
| Adogen 470[4] | 0.70 | 0.60 | 0.93 |
| Adogen 471[5] | 0.05 | 0.15 | 0.07 |
| Decamethyl cyclopentasiloxane/ Polydimethyl Siloxane Gum[3] | 1.67 | 1.67 | 2.33 |
| Amodimethicone (Dow Corning Q2-8220)[6] | 0.10 | 0.10 | 0.10 |
| Surfactant Premix | | | |
| DRO Water | 5.70 | 5.70 | 5.70 |
| Stearalkonium Chloride | 0.30 | 0.30 | 0.30 |

[1]Hydrophobically modified hydroxyethyl cellulose from Aqualon Corp.
[2]Readily dispersible xantham gum
[3]SE-76 gum available From General Electric
[4]Ditallow dimethyl ammonium chloride, Sherex Chemical Co., Dublin, Ohio, USA; 75% aqueous solution
[5]Tallow trimethyl ammonium chloride, Sherex Chemical Co.; 50% aqueous solution.
[6]Trimethylsilylamodimethicone
[7]Polymer in Example 7

The styling polymer premix is prepared by combining the polymer, permethyl 99A, and silicone resin.

The silicone premix is prepared by combining and mixing (in a separate vessel) water, Adogen 470 and Adogen 471 at 85° C. Cool to 71° C. and add the silicone gum/decamethyl cyclopentasiloxane solution and Amodimethicone and mix until homogeneous. Cool to 38° C. while using homogenizer (such as Tekmar).

The surfactant premix is prepared by combining and mixing (in a separate vessel) water and Stearalkonium Chloride at 38° C.

The conditioner premix is prepared by combining and mixing (in a separate vessel) the DRO water heated to 71° C. Citric acid, sodium citrate, cetyl alcohol, stearyl alcohol and Natrosol Plus CS grade D-67 are added and mixed until homogeneous. The xanthan gum is added and mixed until homogeneous. The styling polymer premix, Kathon CG and perfume are added and mixed until homogeneous. The composition is further dispersed with an in-line homogenizer (such as Tekmar homogenizer) and then cooled to 38° C.

The conditioner is completed by combining and mixing (in a separate vessel) the conditioner premix, the silicone premix and the surfactant premix at 38° C. This mixture is then cooled to 38° C.

When the compositions defined in Examples I–III are applied to hair in the conventional manner, they provide effective hair conditioning and styling/hold benefits without leaving the hair with a sticky/stiff feel.

Example 11

Polymer Premix with Added Drying Aid

Prepare the following premix utilizing conventional mixing techniques.

| Ingredients | Weight % |
|---|---|
| Polymer in Example 7 | 16.83 |
| Permethyl 99A | 83.17 |
| Trimethylsiloxysilicate[1] | 1.00 |

[1]As in Example 8.

This mix is prepared by adding the polysiloxane-grafted polymer to the solvents while mixing. Heat to 80–84° C. in a covered vessel, maintaining mixing. Cool to 23–27° C. and add trimethylsiloxysilicate while mixing.

Example 12

Polymer Premix with Added Drying Aid

Prepare the following premix utilizing conventional mixing techniques.

| Ingredients | Weight % |
|---|---|
| Polymer in example 7 | 15.00 |
| Isododecane | 83.50 |
| Polydimethylsiloxane[2] | 1.50 |

[2]Polydimethylsiloxane, Dow Corning, Dow Corning 200 Fluid (20 csk)

This mix is prepared by adding the polysiloxane-grafted polymer to the solvent while mixing. Heat to 80–84° C. in a covered vessel, maintaining mixing. Cool to 23–27° C. and add polydimethylsiloxane while mixing.

Example 13

Polymer Premix with Added Drying Aid

Prepare the following premix utilizing conventional mixing techniques.

| Ingredients | Weight % |
|---|---|
| Polymer in example 7 | 20.00 |
| Linalool | 79.50 |
| Cetyl Dimethicone | 0.50 |

[1]Cetyl Dimethicone, Goldschmidt, Abil Wax 9800

This mix is prepared by adding the polysiloxane-grafted polymer to the solvent while mixing. Heat to 80–84° C. in a covered vessel, maintaining mixing. Add the cetyl dimethicone and cool to 23–27° C. while mixing.

Example 14

Mousse

Mousse compositions are prepared from the following components utilizing conventional mixing techniques.

| | Weight % | | |
|---|---|---|---|
| Ingredients | A | B | C |
| Water | QS 100 | QS 100 | QS 100 |
| Polyquaternium-4[1] | 2.00 | 2.00 | 2.00 |
| Copolymer Premix of Example 12[2] | 10.00 | 8.00 | 12.00 |
| Lauramide DEA | 0.33 | 0.33 | 0.33 |
| Sodium Methyl Oleyl Taurate | 1.67 | 1.67 | 1.67 |
| DMDM Hydantoin | 0.78 | 0.78 | 0.78 |
| Disodium EDTA | 0.20 | 0.20 | 0.20 |
| Polyoxyalkylated isostearyl Alcohol[3] | 0.10 | 0.10 | 0.10 |
| Fragrance | 0.10 | 0.10 | 0.10 |
| Propellant[4] | 7.0 | 7.0 | 7.0 |

[1]Available as Celquat H-100.
[2]Alternatively, mousse compositions are prepared using the Copolymer Premix of Example 11 or 13.
[3]Available as Aerosurf 66-E10.
[4]Available as a mixture of 82.46% isobutane, 16.57% propane, and 0.001% butane.

These products are prepared by first dissolving the Polyquaternium-4 in water with stirring. The remaining ingredients, except the propellant, are then added with stirring.

The resulting mousse concentrate can then be combined with conventional propellants (e.g., Propellant A46) and packaged in an aerosol spray.

These mousses are useful for application to the hair to provide a styling and holding benefit.

Example 15

Hair Tonic

Hair tonic compositions are prepared from the following components utilizing conventional mixing techniques.

| | Weight % | | |
|---|---|---|---|
| Ingredients | A | B | C |
| Permethyl 99A[1] | QS 100 | QS 100 | QS 100 |
| Copolymer of Example 7 | 3.00 | 4.00 | 5.00 |
| Fragrance | 0.10 | 0.20 | 0.30 |

[1]Available from Presperce as isododecane.
[2]Alternatively, tonic compositions are prepared using the Copolymer Premixes of Examples 11 and 12.

These products are prepared by dissolving the cetl hydroxyethylcellulose in the ethanol with stirring and then adding the fragrance and any colors.

These hair tonics are useful for application to the hair to provide a styling and holding benefit.

Example 16

Hair Conditioner

A hair conditioner composition is prepared from the following components utilizing conventional mixing techniques.

| | Weight % | |
|---|---|---|
| Ingredient | A | B |
| Styling Agent Premix | | |
| Copolymer Premix of Example 11[1] | 10.00 | 10.00 |
| Silicone Premix | | |
| Silicone gum, GE SE76[2] | 0.30 | 0.30 |
| Octamethyl cyclotetrasiloxane | 1.70 | 1.70 |
| Main Mix | | |
| Water | QS100 | QS100 |
| Cetyl Alcohol | 1.00 | — |
| Quaternium 18[3] | 0.85 | 0.85 |
| Stearyl Alcohol | 0.70 | — |
| Hydroxethyl Cellulose | 0.50 | — |
| Cetyl Hydroxyethyl Cellulose[4] | — | 1.25 |
| Ceteareth-20 | 0.35 | — |
| Fragrance | 0.20 | 0.20 |
| Dimethicone copolyol | 0.20 | — |
| Citric Acid | 0.13 | 0.13 |
| Methylchloroisothiazolinone (and) methylisothiazolinone | 0.04 | 0.04 |
| Sodium Chloride | 0.01 | 0.01 |
| Xanthan Gum | — | 0.20 |

[1]Alternatively, conditioner compositions are prepared with polymer premixes from Example 12 and 13.
[2]Commercially available from General Electric.
[3]Dimethyl Di(Hydrogenated Tallow) Ammonium Chloride
[4]Commercially avaialbe as Polysurf D-67 from Aqualon.

The product is prepared by comixing all the Main Mix ingredients, heating to about 60° C. with mixing. The mixture is cooled to about 45° C. with colloid milling (Example A) or mixing (Example B). At this temperature, the two premixes are added separately with moderate agitation and the resulting conditioner is allowed to cool to room temperature.

This product is useful as a rinse off hair conditioner.

Example 17

Shampoo Composition

A shampoo composition is prepared from the following components utilizing conventional mixing techniques.

| Ingredient | Weight % |
|---|---|
| Styling Agent | |
| Copolymer Premix from Example 12 | 15.00 |
| Premix | |
| Silicone gum | 0.50 |
| Dimethicone, 350 cs fluid | 0.50 |
| Main Mix | |
| Water | QS 100 |
| Ammonium lauryl sulfate | 11.00 |
| Cocamide MEA | 2.00 |
| Ethylene glycol distearate | 1.00 |
| Xanthan Gum | 1.20 |
| Methylchloroisothiazolinone (and) methylisothiazolinone | 0.04 |
| Citric Acid to pH 4.5 as needed | |

The Main Mix is prepared by first dissolving the xanthan gum in the water with conventional mixing. The remaining Main Mix ingredients are added and the Main Mix is heated to 150° F. with agitation for ½ hour. The Styling Agent and the Premix are then added sequentially with about 10 minutes of agitation between additions, and the entire mixture is stirred while the batch is cooled to room temperature. For varied particle size, the Styling Agent and Premix can be added at different times using either or both high shear mixing (high speed dispersator) or normal agitation.

This shampoos is useful for cleansing the hair and for providing a styling benefit.

What is claimed is:

1. A hair care composition, comprising:
   (A) a nonpolar thermoplastic elastomeric copolymer having a backbone and two or more hydrophobic polymeric side chains, said copolymer formed from the copolymerization of randomly repeating A and B units wherein said copolymer comprises:
      (i) from about 20% to about 90% by weight of said A units, wherein said A units are monomer units copolymerizable with said B units; and
      (ii) from about 10% to about 60% by weight of said B units, wherein said B units are hydrophobic macromonomer units having a polymeric portion and a moiety copolymerizable with said A units,
   wherein said A units, in conjunction with said copolymerizable moieties of said B units form said backbone; wherein said polymeric portion of said B units forms said hydrophobic side chains; wherein said copolymer has a weight average molecular weight greater than about 10,000; wherein said copolymer exhibits at least two distinct $T_g$ values, said first $T_g$ corresponding to said backbone and having a value less than about 0° C., and said second $T_g$ corresponding to said hydrophobic polymeric side chains and having a value greater than about 25° C.; and wherein said B macromonomer units are of the formula:

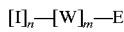

wherein I is a chemical initiator moiety selected from the group consisting of hydrogen, C1–40 straight chain or branched chain alkyl, benzyl, 1-phenyl substituted C2–40 straight chain or branched chain alkyl, 1,1-diphenyl substituted C2–40 straight chain or branched alkyl, and mixtures thereof; n is 0 or 1; W is a hydrophobic monomer unit corresponding to the formula

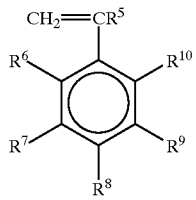

wherein $R^5$ is selected from the group consisting of H and C1–8 straight or branched chain alkyl; $R^6$, $R^7$, $R^8$, $R^9$, and $R^{10}$ are independently selected from the group consisting of C1–C8 straight or branched chain alkyl such that each of $R^6$, $R^7$, $R^8$, $R^9$, and $R^{10}$ are not simultaneously H; m is an integer from about 10 to about 2000; and E is an ethylenically unsaturated endcapping moiety, copolymerizable with A and C, selected from the group consisting of vinyl, allyl, acryloyl, methacryloyl, ethacryloyl, 2-vinyl benzyl, 3-vinyl benzyl, 4-vinyl benzyl, 2-vinyl benzoyl, 3-vinyl benzoyl, 4-vinyl benzoyl, 1-butenyl, 1-propenyl, isobutenyl, isoprenyl, cyclohexenyl, cyclopentenyl, and mixtures thereof;

(B) a water-insoluble, volatile solvent for said copolymer suitable for application to the hair; and
   (C) a carrier suitable for delivery of said copolymer and said solvent to the hair.

2. The composition according to claim 1 wherein said nonpolar thermoplastic elastic copolymer additionally comprising from about 0% to about 20% by weight of randomly repeating C units, wherein said C units are polysiloxane macromonomer units having a polymeric portion and a moiety copolymerizable with said A and B units, and wherein said A units, in conjunction with said copolymerizable moieties of said B units and said C units, form said backbone.

3. A composition according to claim 2 wherein said A monomer units are ethylenically unsaturated monomer units, said B macromonomer units are units having a polymeric portion and an ethylenically unsaturated moiety that is copolymerizable with said A and C units, said C macromonomer units are units having a polymeric portion and an ethylenically unsaturated moiety that is copolymerizable with said A and B units, and said copolymer has a weight average molecular weight from about 10,000 to about 5,000,000.

4. A composition according to claim 3 wherein the $T_g$ corresponding to said backbone is from about −45° C. to about −120° C., and the $T_g$ corresponding to said hydrophobic polymeric side chains is from about 35° C. to about 150° C.

5. A composition according to claim 4 wherein said A monomer units are selected from the group consisting of acrylic acid esters, N-alkyl acrylamides, alkyl vinyl ethers, alkyl substituted styrenes, and mixtures thereof.

6. A composition according to claim 5 wherein said acrylic acid ester corresponds to the following formula

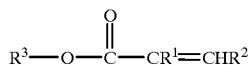

wherein $R^1$ and $R^2$ are independently selected from the group consisting of H, $C_1$–$C_8$ straight chain or branched chain alkyl, methoxy, ethoxy, 2-hydroxyethoxy, 2-methoxyethyl, and 2-ethoxyethyl, and $R^3$ is selected from the group consisting of $C_1$–$C_{30}$ straight chain, branched chain, or cyclic alkyl; chloro and/or fluoro substituted $C_1$–$C_{30}$ straight chain, branched chain or cyclic alkyl; phenyl substituted $C_1$–$C_{30}$ straight chain, branched chain, or cyclic alkyl; methoxy, ethoxy, and phenoxy substituted $C_1$–$C_{30}$ straight chain, branched chain, or cyclic alkyl; and cyano substituted $C_1$–$C_{30}$ straight chain, branched chain, or cyclic alkyl.

7. A composition according to claim 5 wherein said acrylic acid ester is selected from the group consisting of octadecyl acrylate, tetradecyl acrylate, nonyl acrylate, ethylbutyl acrylate, ethyl acrylate, 2-ethylhexyl acrylate, hexadecyl acrylate, hexyl acrylate, and mixtures thereof.

8. A composition according to claim 5 wherein said N-alkyl acrylamide corresponds to the following formula

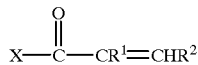

wherein $R^1$ and $R^2$ are independently selected from the group consisting of H, $C_1$–$C_8$ straight chain or branched chain alkyl, methoxy, ethoxy, 2-hydroxyethoxy, 2-methoxyethyl, and 2-ethoxyethyl, and X is selected from the group consisting of —NHR$^4$, and —N(R$^4$)$_2$ wherein each R$^4$ is independently selected from the group consisting of C$_1$–C$_{30}$ straight chain or branched chain alkyl.

9. A composition according to claim 5 wherein said alkyl vinyl ether corresponds to the following formula

R$^3$—O—CR$^1$=CHR$^2$ wherein R$^1$ and R$^2$ are independently selected from the group consisting of H, C$_1$–C$_8$ straight chain or branched chain alkyl, methoxy, ethoxy, 2-hydroxyethoxy, 2-methoxyethyl, and 2-ethoxyethyl, and R$^3$ is selected from the group consisting of C$_1$–C$_{30}$ straight chain, branched chain, or cyclic alkyl; chloro and/or fluoro substituted C$_1$–C$_{30}$ straight chain, branched chain or cyclic alkyl; phenyl substituted C$_1$–C$_{30}$ straight chain, branched chain, or cyclic alkyl; methoxy, ethoxy, and phenoxy substituted C$_1$–C$_{30}$ straight chain, branched chain, or cyclic alkyl; and cyano substituted C$_1$–C$_{30}$ straight chain, branched chain, or cyclic alkyl.

10. A composition according to claim 5 wherein said alkyl substituted styrene corresponds to the following formula

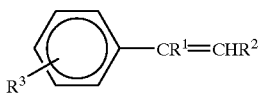

wherein R$^1$ and R$^2$ are independently selected from the group consisting of H, C$_1$–C$_8$ straight chain or branched chain alkyl, methoxy, ethoxy, 2-hydroxyethoxy, 2-methoxyethyl, and 2-ethoxyethyl, and R$^3$ is selected from the group consisting of C$_1$–C$_{30}$ straight chain, branched chain, or cyclic alkyl; chloro and/or fluoro substituted C$_1$–C$_{30}$ straight chain, branched chain or cyclic alkyl; phenyl substituted C$_1$–C$_{30}$ straight chain, branched chain, or cyclic alkyl; methoxy, ethoxy, and phenoxy substituted C$_1$–C$_{30}$ straight chain, branched chain, or cyclic alkyl; and cyano substituted C$_1$–C$_{30}$ straight chain, branched chain, or cyclic alkyl.

11. A composition according to claim 9 wherein n is 1, and said chemical initiator moiety I is selected from the group consisting of 1,1-diphenyl-4-methylpentyl, sec-butyl, and mixtures thereof.

12. A composition according to claim 11 wherein W is selected from the group consisting of 4-t-butyl vinyl benzene, 2,4-dimethyl vinyl benzene, 4-(2-ethylhexyl) vinyl benzene, and mixtures thereof.

13. A composition according to claim 9 wherein said polysiloxane macromonomer is of the formula

E'(Y)$_w$Si(R$^{11}$)$_{3-t}$(Z)$_t$ wherein E' is an ethylenically unsaturated moiety copolymerizable with A and B; Y is a divalent linking group; R$^{11}$ is selected from the group consisting of H, lower alkyl, aryl, or alkoxy; Z is a monovalent siloxane polymeric moiety having a number average molecular weight of at least about 500, is essentially unreactive under copolymerization conditions, and is pendant from said backbone after polymerization; w is 0 or 1; and t is an integer from 1 to 3.

14. A composition according to claim 13 wherein said polysiloxane macromonomer is selected from the group consisting of

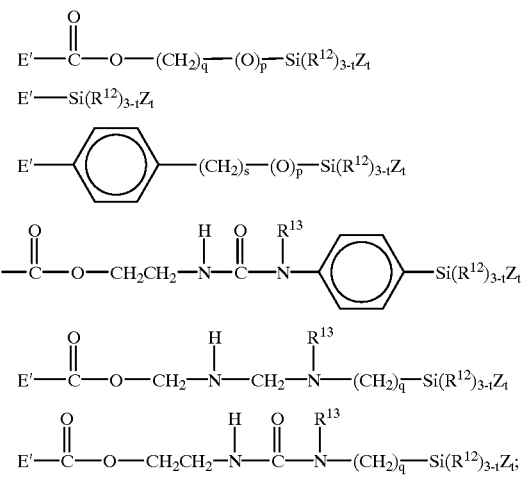

wherein t is 1, 2, or 3; p is 0 or 1; R$^{13}$ is allyl or hydrogen; q is an integer from 2 to 6, s is an integer from 0 to 2; E' is

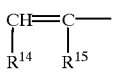

wherein R$^{14}$ is hydrogen or —COOH; R$^{15}$ is hydrogen, methyl or —CH$_2$COOH; Z is

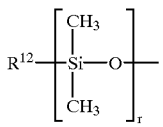

wherein R$^{12}$ is alkyl, alkoxy, alkylamino, aryl, or hydroxyl; and r is an integer from about 5 to about 700.

15. A composition according to claim 1 comprising from about 0.1% to about 25% of said copolymer.

16. A composition according to claim 15 comprising from about 0.1% to about 50% of said water insoluble volatile solvent.

17. A composition according to claim 16 wherein said water insoluble volatile solvent is selected from the group consisting of silicone fluids, silane fluids, hydrocarbons, esters, ethers, alcohols, and mixtures thereof.

18. A hair care composition, comprising:
(A). a thermoplastic elastomeric copolymer having a backbone and two or more hydrophobic polymeric side chains, said copolymer formed from the copolymerization of randomly repeating A, B, and C units and corresponding to the formula

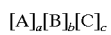
[A]$_a$[B]$_b$[C]$_c$ wherein
(i) A is at least one monomer unit copolymerizable with B and C; selected from the group consisting of acrylic acid esters, N-alkyl acrylamides, alkyl vinyl ethers, alkyl substituted styrenes, and mixtures thereof; and a is an integer of about 100 or greater;
(ii) B is at least one nonpolar, hydrophobic macromonomer unit copolymerizable with A and C corresponding to the formula

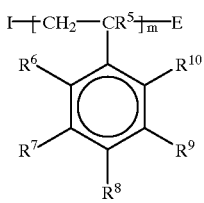

wherein I is selected from the group consisting of hydrogen, C1–40 straight or branched chain alkyl, benzyl, 1-phenyl substituted C2–40 straight or branched chain alkyl, 1,1-diphenyl substituted C2–40 straight or branched chain alkyl, and mixtures thereof; $R^5$ is selected from the group consisting of H and C1–C8 alkyl; $R^6$, $R^7$, $R^8$, $R^9$, and $R^{10}$ are independently selected from the group consisting of C1–C8 straight or branched chain alkyl such that each of $R^6$, $R^7$, $R^8$, $R^9$, and $R^{10}$ are not simultaneously H; m is an integer from about 10 to about 2000; and E is an ethylenically unsaturated moiety, copolymerizable with A and C, selected from the group consisting of vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, cyclohexenyl, cyclopentenyl, and mixtures thereof; and b is an integer of about 2 or greater; and (iii) C is a polysiloxane macromonomer unit copolymerizable with A and B corresponding to the formula $E'(Y)_w Si(R^{11})_{3-t}(Z)_t$ wherein E' is an ethylenically unsaturated moiety copolymerizable with A and B; Y is a divalent linking group; $R^{11}$ is selected from the group consisting of H, lower alkyl, aryl, or alkoxy; Z is a monovalent siloxane polymeric moiety having a number average molecular weight of at least about 500, is essentially unreactive under copolymerization conditions, and is pendant from said backbone after polymerization; w is 0 or 1; t is an integer from 1 to 3; and c is an integer of zero or greater; and (B). a water insoluble volatile solvent for said copolymer suitable for application to the hair.

19. A method for styling hair comprising applying an effective amount of the composition of claim 1 to the hair.

20. A method for conditioning hair comprising applying an effective amount of the composition of claim 1 to the hair.

21. The composition of claim 1 wherein said first $T_g$ corresponding to said backbone has a value less than about $-20°$ C.

22. The composition of claim 1 wherein said solvent is selected from the group consisting of cyclic volatile silicone fluids, linear volatile silicone fluids, volatile silane liquids, straight chain hydrocarbons having from about 10 to about 16 carbon atoms, branched chain hydrocarbons having from about 10 to about 16 carbon atoms, alkyl alcohols, methyl alkanoates, alkyl acetates, benzoates, di ($C_5$–$C_7$) alkyl ethers, and mixtures thereof.

23. The composition of claim 22 wherein said solvent is selected from the group consisting of cyclic silicone fluids.

24. The composition of claim 22 wherein said solvent is selected from the group consisting of branched chain hydrocarbons having from about 10 to about 16 carbon atoms.

* * * * *